(12) United States Patent
Pilch et al.

(10) Patent No.: US 7,297,327 B2
(45) Date of Patent: Nov. 20, 2007

(54) ORAL CARE MALODOR COMPOSITION

(75) Inventors: Shira Pilch, Highland Park, NJ (US); Malcolm Williams, Piscataway, NJ (US); Joe Vazquez, Hamilton Township, NJ (US)

(73) Assignee: Colgate-Palmolive Company, New York, NY (US)

( * ) Notice: Subject to any disclaimer, the term of this patent is extended or adjusted under 35 U.S.C. 154(b) by 358 days.

(21) Appl. No.: 11/020,009

(22) Filed: Dec. 21, 2004

(65) Prior Publication Data

US 2006/0134023 A1    Jun. 22, 2006

(51) Int. Cl.
  *A61K 8/97*  (2006.01)
  *A61K 36/00*  (2006.01)
  *A61K 36/53*  (2006.01)
  *A61K 36/13*  (2006.01)

(52) U.S. Cl. .................. 424/58; 424/725; 424/745; 424/770

(58) Field of Classification Search .............. None
  See application file for complete search history.

(56) References Cited

U.S. PATENT DOCUMENTS

| | | | |
|---|---|---|---|
| 4,423,030 A | 12/1983 | Hayes et al. | |
| 4,512,741 A | 4/1985 | Mushta | |
| 4,960,597 A | 10/1990 | Farbood et al. | |
| 5,182,101 A | 1/1993 | Wuelknitz et al. | |
| 5,320,862 A | 6/1994 | La Tona | |
| 5,939,050 A * | 8/1999 | Iyer et al. | 424/49 |
| 5,942,211 A * | 8/1999 | Harper et al. | 424/49 |
| 6,248,309 B1 * | 6/2001 | Iyer et al. | 424/49 |
| 6,294,161 B1 | 9/2001 | Hiramoto et al. | |
| 6,322,838 B1 | 11/2001 | Güntert et al. | |
| 6,375,933 B1 | 4/2002 | Subramanyam et al. | |
| 6,379,652 B1 | 4/2002 | Liu et al. | |
| 6,518,227 B2 | 2/2003 | Woosley | |
| 6,680,289 B1 | 1/2004 | Woo et al. | |
| 6,689,342 B1 | 2/2004 | Pan et al. | |
| 6,733,798 B2 | 5/2004 | Heeg et al. | |
| 6,740,311 B2 | 5/2004 | White, Jr. et al. | |
| 6,790,465 B2 * | 9/2004 | Weissman | 424/750 |
| 2003/0206874 A1 | 11/2003 | Doyle et al. | |
| 2006/0024248 A1 * | 2/2006 | Spengler et al. | 424/49 |
| 2006/0263475 A1 * | 11/2006 | Jani et al. | 426/3 |

FOREIGN PATENT DOCUMENTS

| | | |
|---|---|---|
| CH | 688985 | 7/1998 |
| GB | 191029565 | 2/1911 |
| JP | 59-175410 | * 10/1984 |
| WO | WO 03/105794 | 12/2003 |

OTHER PUBLICATIONS

Leung, A.Y., "Encyclopedia of Common and Natural Ingredients Used in Food, Drug and Cosmetics". 1998. pp. 36-38, 68-69, 240-243, 325-327, 492-494.

* cited by examiner

*Primary Examiner*—Christopher R. Tate
(74) *Attorney, Agent, or Firm*—Kristyne A. Bullock

(57) ABSTRACT

An oral odor control agent admixture of generally equivalent proportions of thymol, anise, fennel, basil, and juniperberry essential oils shows efficacy as an odor control agent in oral care for control of garlic odor.

21 Claims, No Drawings

ORAL CARE MALODOR COMPOSITION

The present invention relates to a dentifrice composition useful for reducing oral malodor. In particular, the present invention includes dentifrices incorporating a malodor agent containing thymol, anise, fennel, basil, and juniperberry essential oils.

Many individuals desire a "bright" smile, healthy teeth, and a pleasant personal presence in social interactions. Unfortunately, some foods, while enjoyable when consumed, deposit and/or transfer chemical compounds into the oral cavity or into the blood stream that linger to afflict the social presence of a person with malodor during exhalation accompanying conversation and/or respiration. This malodor generally detracts from the desired pleasant social presence. Garlic and onion containing foods are especially of concern in this regard and have frustrated long term efficacy in malodor remedies.

SUMMARY

The present invention provides oral care compositions. In somewhat greater detail, the invention is for an oral odor control agent composition, comprising:
  (a) from about 10 weight percent to about 30 weight percent thymol essential oil;
  (b) from about 10 weight percent to about 30 weight percent anise essential oil;
  (c) from about 10 weight percent to about 30 weight percent fennel essential oil;
  (d) from about 10 weight percent to about 30 weight percent basil essential oil; and
  (e) a remainder of juniperberry essential oil wherein said juniperberry essential oil is from about 10 weight percent to about 30 weight percent of said oral admixture composition.

In one aspect, the oral control agent is provided in from about 0.3 weight percent to about 2 weight percent of an oral care vehicle in a product such as mouthwash, dental cream, or toothpaste. In another aspect, the oral control agent is provided in a lozenge or other portable form such as a mint, bead, wafer, liquid formulated for oral application from a small portable nebulizer (spray bottle), liquid formulated for oral application from a small portable drop-generating bottle, or a soft pliable tablet ("chewie").

The invention is also for admixing an oral control agent into an oral care vehicle according to any of the above-described formulations.

In another aspect, the invention provides a method for suppressing malodor by applying the above formulation to the oral cavity.

It has been discovered that compositions and methods of this invention afford advantages over oral care compositions among known in the art.

Further areas of applicability will become apparent from the detailed description provided hereinafter. It should be understood that the detailed description and specific examples, while indicating embodiments of the invention, are intended for purposes of illustration only and are not intended to limit the scope of the invention.

DESCRIPTION

The following definitions and non-limiting guidelines must be considered in reviewing the description of this invention set forth herein. The headings (such as "Introduction" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

Compositions

The present invention provides an oral care composition having an odor control agent (malodor oral care) composition and methods for administration or application to, or use with, a human or other animal subject. In overview, the oral care composition and odor control agent composition is achieved with an odor control admixture comprising thymol, anise, fennel, basil, and juniperberry essential oils.

As referred to herein, an "oral care composition" is any composition that is suitable for administration or application to the oral cavity of a human or animal subject for enhancing the health, hygiene or appearance of the subject, preferably providing such benefits as: the prevention or treatment of a condition or disorder of the teeth, gums, mucosa or other hard or soft tissue of the oral cavity; the prevention or treatment of a systemic condition or disorder; the provision of sensory, decorative or cosmetic benefits; and combinations thereof. In various embodiments, an oral care composition is not intentionally swallowed, but is rather retained in the oral cavity for a time sufficient to effect the intended utility. In other portable embodiments (such as a lozenge, mint, bead, wafer, liquid formulated for oral application from a small portable nebulizer, liquid formulated for oral application from a small portable drop-generating bottle, or a soft pliable tablet), an oral care composition is intentionally swallowed, optionally after retention in the oral cavity for a time sufficient to effect intended utility. Preferably, specific materials and compositions to be used in this invention are, accordingly, pharmaceutically- or cosmetically-acceptable, clinically effective, and/or clinically efficacious. As used herein, such a "pharmaceutically acceptable" or "cosmetically acceptable", "clinically effective", and/or "clinically efficacious" component is one that is suitable for use with humans and/or animals and is provided in an appropriate amount (a clinically efficacious amount) to provide the desired therapeutic, prophylactic, sensory, decorative, or cosmetic benefit without undue adverse side effects (such as toxicity, irritation, and allergic response) commensurate with a reasonable benefit/risk ratio.

Orally Acceptable Carrier

The present invention provides compositions comprising an orally acceptable carrier in a product such as mouthwash, toothpaste, dental cream, or portable dosage article such as, without limitation, a lozenge, a mint, bead, wafer, liquid formulated for oral application in a small portable nebulizer (spray bottle), liquid formulated for oral application in a small portable drop-generating bottle, or a soft pliable tablet ("chewie"). As used herein, an "orally acceptable carrier" refers to a material or combination of materials that are safe for use in the compositions of the present invention, commensurate with a reasonable benefit/risk ratio, with which the blended thymol, anise, fennel, basil, and juniperberry essential oils may be associated while retaining significant efficacy. Preferably, the carrier does not substantially reduce the efficacy of the blended thymol, anise, fennel, basil, and juniperberry essential oils.

Materials among those that are useful in carriers include adhesion agents, surfactants, foam modulators, abrasives, pH modifying agents, humectants, mouth feel agents, sweeteners, flavorants, colorants, and combinations thereof. It is understood that while general attributes of each of the above categories of materials may differ, there may be some common attributes and any given material may serve multiple purposes within two or more of such categories of materials. Preferably, such carrier materials are selected for compatibility with blended thymol, anise, fennel, basil, and juniperberry essential oils and with other ingredients of the composition.

Mouth-feel agents include materials imparting a desirable texture or other feeling during use of the composition. Such agents include dispersed flavorants and sweeteners.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1, 2-diol, cinnamaldehyde glycerol acetal (CGA), methone glycerol acetal (MGA), and mixtures thereof. One or more flavorants are optionally present in a total amount of about 0.01% to about 5%, optionally in various embodiments from about 0.05 to about 2%, from about 0.1% to about 2.5%, and from about 0.1 to about 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5%, optionally from about 0.01% to about 1%.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20%, for example about 0.01% to about 10% or about 0.1% to about 5%.

Active Material

In a preferred embodiment, an oral odor control agent admixture composition is provided as an essential oil admixture. The admixture comprises:
  (a) from about 10 weight percent to about 30 weight percent (preferably 20 weight percent) thymol essential oil;
  (b) from about 10 weight percent to about 30 weight percent (preferably 20 weight percent) anise essential oil;
  (c) from about 10 weight percent to about 30 weight percent (preferably 20 weight percent) fennel essential oil;
  (d) from about 10 weight percent to about 30 weight percent (preferably 20 weight percent) basil essential oil; and
  (e) from about 10 weight percent to about 30 weight percent (preferably 20 weight percent) of juniperberry essential oil.

In one embodiment, the admixture comprises a remainder of juniperberry essential oil where the juniperberry essential oil is from about 10 weight percent to about 30 weight percent (preferably 20 weight percent) of the oral admixture composition. In one embodiment, the present invention provides a composition consisting essentially of a carrier and an admixture that consists essentially of thymol essential oil, anise essential oil, fennel essential oil, basil essential oil, and juniperberry essential oil, at the concentrations set forth above. In various embodiments, such compositions consisting essentially of the admixture do not contain significant levels of other essential oils.

In this regard, a surprising result (see the Examples) shows that this particular mixture of thymol, anise, fennel, basil, and juniperberry essential oils provides especial efficacy in reducing garlic odor in human testing. This surprising find surmounts the traditional challenge of controlling complex and systemically sustained garlic odor and onion odor. Actives such as copper chlorophyllin and parsley seed oil have traditionally been used to control garlic malodor. However, a mixture embodiment of thymol, anise, fennel, basil, and juniperberry essential oils in equivalent parts shows a surprisingly dramatic reduction of nearly 80 percent in garlic malodor.

In one embodiment, each of the thymol, anise, fennel, and basil essential oils are independently from about 15 weight percent to about 25 weight percent of the composition. In one embodiment, each of the thymol, anise, fennel, and basil essential oils are independently about 20 weight percent of the odor control agent in the oral care composition.

In one embodiment, the oral odor control agent admixture provides from about 0.3 weight percent to about 2 weight percent of an oral care composition in an oral care vehicle. In one embodiment, the oral care vehicle and oral odor control agent admixture is toothpaste. In an alternative embodiment, the oral care vehicle and oral odor control agent admixture is dental cream. In a further alternative embodiment, the oral care vehicle and oral odor control agent admixture is mouthwash. In yet another embodiment, liquid oral care vehicle and oral odor control agent admixture is a lozenge where the oral care vehicle and oral odor control agent admixture is infused, in one embodiment, into a shell or capsule. In another embodiment, liquid oral care vehicle and oral odor control agent admixture is intermixed into a oral paste that is dried into the lozenge. The lozenge dissolves into an oral care vehicle in the oral cavity upon contact with water in saliva. As should be apparent, a similar infusing and/or admixing procedure is also used in making further portable form alternative embodiments such as, without limitation, a mint, bead, wafer, liquid formulated for oral application from a small portable nebulizer (spray bottle), liquid formulated for oral application from a small portable drop-generating bottle, or a soft pliable tablet ("chewie").

In addition to the malodor (malodour) control agent described in detail herein, the compositions of the present invention optionally comprise other active materials, operable for the prevention or treatment of a condition or disorder of hard or soft tissue of the oral cavity, the prevention or treatment of a physiological disorder or condition, or to provide a cosmetic benefit in any of the mouthwash, dental cream, toothpaste, or lozenge (as well as in other portable form embodiments as previously described herein) formulations. In various embodiments, the active is a "systemic active" which is operable to treat or prevent a disorder that, in whole or in part, is not a disorder of the oral cavity. In various embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, tooth desensitizers, salivary stimulants, and combinations thereof. It is understood that while general attributes of each of the above categories of actives may differ, there may some common attributes and any given material may serve multiple purposes within two or more of such categories of actives and that the optional active does not confound efficacy of the thymol, anise, fennel, basil, and juniperberry blended essential oil malodour control agent described in detail herein.

Actives useful herein are present in the compositions of the present invention in safe and effective amounts. A "safe and effective" and "clinically efficacious" amount of an active is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific safe and effective ("clinically efficacious") amount of the active will vary with such factors as the particular condition being treated, the physical condition of the subject, the nature of concurrent therapy (if any), the specific active used, the specific dosage form, the carrier employed, and the desired dosage regimen.

The compositions of the present invention further comprise an optional abrasive formulated to not confound efficacy of the thymol, anise, fennel, basil, and juniperberry blended essential oil malodour control agent described in detail herein. In various embodiments, an additional optional abrasive is useful for example as a polishing agent. Any orally acceptable abrasive can be used, but type, fineness, (particle size) and amount of abrasive should be selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

The compositions of the present invention optionally comprise a tartar control (anticalculus) agent formulated to not confound efficacy of the thymol, anise, fennel, basil, and juniperberry blended essential oil malodour control agent described in detail herein. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

The compositions of the present invention optionally comprise a fluoride ion source formulated to not confound efficacy of the thymol, anise, fennel, basil, and juniperberry blended essential oil malodour control agent described in detail herein and useful, for example, as an anti-caries agent. Any orally acceptable particulated fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof. One or more fluoride ion sources are optionally present in an amount providing a clinically efficacious amount of soluble fluoride ion to the oral care composition.

The compositions of the present invention optionally comprise a saliva stimulating agent formulated to not confound efficacy of the thymol, anise, fennel, basil, and juniperberry blended essential oil malodour control agent described in detail herein and useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

The compositions of the present invention optionally comprise a nutrient formulated to not confound efficacy of the thymol, anise, fennel, basil, and juniperberry blended essential oil malodour control agent described in detail herein. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

Methods of Manufacture

The above-described compositions of the present invention are made by methods; these methods include admixing thymol, anise, fennel, basil, and juniperberry essential oils as described above to yield an odor control agent. The odor control agent is then admixed into an oral care vehicle to provide a formulation such as mouthwash, toothpaste, dental cream, or a lozenge (or into another portable form embodiment as previously described herein so that the odor control agent and oral carrier in admixture provide a portable dose article such as, without limitation, a lozenge, a mint, a bead, a wafer, a small portable nebulizer containing liquid formulated for oral application as a spray, a small portable bottle containing liquid formulated for oral application as a drop, or a soft pliable "chewie" tablet) through traditional processes for making these formulations as traditionally practiced by those of skill.

In an alternative embodiment, thymol, anise, fennel, basil, and juniperberry essential oils are independently admixed into an oral care vehicle to provide a formulation—such as mouthwash, toothpaste, dental cream, or a lozenge (or another portable form embodiment as previously described herein so that a virtually provided odor control agent and oral carrier in admixture provide a portable dose article such as, without limitation, a lozenge, a mint, a bead, a wafer, a small portable nebulizer containing liquid formulated for oral application as a spray, a small portable bottle containing liquid formulated for oral application as a drop, or a soft pliable "chewie" tablet)—having an effective odor control agent as described above. As is appreciated by those of skill, the odor control agent is thereby virtually admixed in this alternative method embodiment even though not initially admixed from the thymol, anise, fennel, basil, and juniperberry essential oils as a separate formulation.

Methods of Use

The present invention provides methods for cleaning a tooth surface using compositions according to the present invention. As referred to herein, "tooth" or "teeth" refers to natural teeth, dentures, dental plates, fillings, caps, crowns, bridges, dental implants, and the like, and any other hard surfaced dental prosthesis either permanently or temporarily fixed within the oral cavity.

Accordingly, the present invention provides methods for cleaning a tooth surface, comprising applying to the surface a safe and effective amount of dentifrice (such as, without limitation, toothpaste, or dental cream) or mouthwash where the dentifrice or mouthwash contains an effective (clinically efficacious) amount of the odor control agent and then either agitating the dentifrice against each surface of the tooth with a toothbrush or agitating the mouthwash against the teeth by vigorous swishing. As referred to herein, "applying" refers to any method by which the dentifrice or mouthwash is placed in contact with the tooth surface. Such methods, in various embodiments, comprise direct application of a composition by such methods as painting and brushing. In various embodiments, application of the composition comprises the use of an application device, which aids in maintaining contact of the composite to the tooth surface for sufficient time so as to allow cleaning.

The present invention also provides methods for suppressing malodor by using compositions according to the present invention, comprising (a) ingesting into the oral cavity a safe and effective amount of formulated dosage of the odor control agent admixture embodiments described herein from a portable dose article such as, without limitation, a lozenge, a mint, a bead, a wafer, a small portable nebulizer containing liquid formulated for oral application as a spray, a small portable bottle containing liquid formulated for oral application as a drop, or a soft pliable "chewie" tablet, (b) optionally retaining the dosage within the oral cavity for a period of time, and (c) swallowing the dosage.

In various embodiments, it is preferred that the subject does not eat or drink while the dentifrice and/or mouthwash oral care composition is in contact with the dental surface. The oral care composition can be removed as and when required, at will, by an employment of standard oral hygiene procedures such as brushing or by rinsing, e.g., with water. The process can be repeated several times until the desired cleaning results are achieved.

In various embodiments, compositions of the present invention are also used for the treatment or prevention of disorders in the oral cavity, including cavity prevention, whitening, plaque prevention or reduction, gingivitis prevention or reduction, tartar control, sensitivity prevention or reduction, breath malodor prevention or reduction, and stain prevention. Compositions of the present invention may also be used for the treatment or prevention of systemic disorders, such as the improvement of overall systemic health characterized by a reduction in risk of development of systemic diseases, such as cardiovascular disease, stroke, diabetes, severe respiratory infection, premature and low birth weight infants (including associated post-partum dysfunction in neurologic/developmental function), and associated increased risk of mortality. Such methods include those disclosed in U.S. Patent Publication 2003/0206874, Doyle et al., published Nov. 6, 2003.

The present invention is further illustrated through the following non-limiting examples.

EXAMPLE 1

In vitro screening of various natural extracts to control garlic is achieved by treating a garlic-saliva mixture with the test extract for at least 8 hours (overnight) in an enclosed container and analyzing the headspace of the container by gas chromatography at settings suitable for garlic detection. The garlic-saliva mixture is prepared as a 1:1 ratio of one part whole saliva and one part of 1 weight percent garlic water extract. The garlic-saliva mixture is treated with the test extract and incubated at 37 degrees Celsius overnight. The results of the study are shown in Table 1.

TABLE 1

| Active | Total garlic odor in ppb | Percent reduction in garlic odor |
| --- | --- | --- |
| Negative Control (water treated) | 1800 | N/A |
| Anise star | 90.1 | 95.0 |
| Basil | 90.7 | 95.0 |
| Dillseed | 90.1 | 95.0 |
| Sweet fennel | 91.2 | 94.9 |
| Juniperberry | 91.1 | 94.9 |
| Parsley | 90.5 | 95.0 |
| Rosemary | 88.9 | 95.0 |
| Sage | 85.9 | 95.2 |
| Camphor | 81.0 | 95.5 |
| Cinnamon | 84.9 | 95.3 |
| Clove | 78.6 | 95.6 |
| Neroli | 91.0 | 94.9 |
| Pine | 91.6 | 94.9 |
| Thyme | 90.8 | 95.0 |
| Saffron | 95.7 | 94.7 |
| Lemongrass | 87.3 | 95.1 |
| Flaxseed | 1026 | 43.2 |
| Jojoba | 1188 | 34.1 |
| Cottonseed | 1452 | 19.3 |

As shown in Table 1, anise star, basil, dill seed, sweet fennel, juniperberry, lemongrass, parsley, rosemary, sage, camphor, cinnamon, clove, neroli, pine, saffron, and thyme extracts all show significant efficacy in reducing garlic odor when used at less than 0.13 weight percent levels in the test.

EXAMPLE 2

The best-performing odor control actives of Example 1 are tested in combination to explore synergistic effects using the technique of Example 1. A control of a traditional garlic odor oral care active blend is also tested according to the same technique. The five actives of thymol, anise, fennel, basil, and juniperberry essential oils, when combined at a ratio of 1:1:1:1:1 (20 weight percent each respective to the odor control active test formulation) indicate the most effective additive and/or synergistic effect of all combinations. Quantitative garlic odor efficacy for the thymol, anise, fennel, basil, and juniperberry essential oils blend in ratio of 1:1:1:1:1 indicates a 78 percent reduction in garlic odor components in the test headspace. Quantitative garlic odor efficacy for the control (the traditional garlic odor oral care active blend) indicates a 53 percent reduction in garlic odor components in the test headspace. The results indicate a surprising efficacy for the thymol, anise, fennel, basil, and juniperberry essential oils blend in 1:1:1:1:1 blending.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. An oral odor control agent admixture composition, comprising:
   (a) from about 10 weight percent to about 30 weight percent thymol essential oil;
   (b) from about 10 weight percent to about 30 weight percent anise essential oil;
   (c) from about 10 weight percent to about 30 weight percent fennel essential oil;
   (d) from about 10 weight percent to about 30 weight percent basil essential oil; and
   (e) from about 10 weight percent to about 30 weight percent of juniperberry essential oil.

2. A composition according to claim 1 wherein each of said thymol, anise, fennel, and basil essential oils are independently from about 15 weight percent to about 25 weight percent of said composition.

3. A composition according to claim 1 wherein each of said thymol, anise, fennel, and basil essential oils are independently about 20 weight percent of said composition.

4. An oral care composition comprising:
   (a) an oral care vehicle; and
   (b) from about 0.3 weight percent to about 2 weight percent oral odor control agent dispersed in said oral care vehicle, said odor control agent comprising essential oils in respective proportions to said odor control agent of
      (1) from about 10 weight percent to about 30 weight percent thymol essential oil,
      (2) from about 10 weight percent to about 30 weight percent anise essential oil,
      (3) from about 10 weight percent to about 30 weight percent fennel essential oil,
      (4) from about 10 weight percent to about 30 weight percent basil essential oil, and (5) a remainder of juniperberry essential oil wherein said juniperberry essential oil is from about 10 weight percent to about 30 weight percent of said odor control agent.

5. A composition according to claim 4 wherein said oral care vehicle is an oral care vehicle for toothpaste.

6. A composition according to claim 4 wherein said oral care vehicle is an oral care vehicle for dental cream.

7. A method for making an oral odor control formulation for diminishing garlic malodor, comprising:
 (a) admixing thymol, anise, fennel, basil, and juniperberry essential oils to comprise an odor control agent of
  (1) from about 10 weight percent to about 30 weight percent thymol essential oil,
  (2) from about 10 weight percent to about 30 weight percent anise essential oil,
  (3) from about 10 weight percent to about 30 weight percent fennel essential oil,
  (4) from about 10 weight percent to about 30 weight percent basil essential oil, and
  (5) a remainder of juniperberry essential oil wherein said juniperberry essential oil is from about 10 weight percent to about 30 weight percent of said oral admixture composition; and
 (b) admixing an orally effective proportion of said odor control agent with an oral care vehicle.

8. An oral odor control formulation made by a process according to the method of claim 7.

9. A method according to claim 7 wherein said admixing an orally effective proportion admixes said oral care vehicle and said odor control agent to provide toothpaste.

10. Toothpaste made by a process according to the method of claim 9.

11. A method according to claim 7 wherein said admixing an orally effective proportion admixes said oral care vehicle and said odor control agent to provide dental cream.

12. Dental cream made by a process according to the method of claim 11.

13. A method according to claim 7 wherein said admixing an orally effective proportion admixes said oral care vehicle and said odor control agent to provide a portable dose article selected from the group consisting of a lozenge, a mint, a bead, a wafer, liquid formulated for oral application as a spray from a small portable nebulizer, liquid formulated for oral application as a drop from a small portable bottle, and a soft pliable tablet.

14. A portable dose article made by a process according to the method of claim 13, said portable dose article selected from the group consisting of a lozenge, a mint, a bead, a wafer, a small portable nebulizer containing said admixture in liquid formulated for oral application as a spray, a small portable bottle containing said admixture in liquid formulated for oral application as a drop, and a soft pliable tablet.

15. A method according to claim 7 wherein said admixing an orally effective proportion admixes said oral care vehicle and said odor control agent to provide mouthwash.

16. Mouthwash made by a process according to the method of claim 15.

17. A method for suppressing oral malodor, comprising: applying to the oral cavity an oral care vehicle having an orally effective amount of a dispersed odor control agent, said odor control agent comprising essential oils in respective proportions to said odor control agent of:
 (1) from about 10 weight percent to about 30 weight percent thymol essential oil;
 (2) from about 10 weight percent to about 30 weight percent anise essential oil;
 (3) from about 10 weight percent to about 30 weight percent fennel essential oil;
 (4) from about 10 weight percent to about 30 weight percent basil essential oil; and
 (5) a remainder of juniperberry essential oil wherein said juniperberry essential oil is from about 10 weight percent to about 30 weight percent of said odor control agent.

18. A method according to claim 17 wherein said oral care vehicle and said dispersed odor control agent are comprised in toothpaste.

19. A method according to claim 17 wherein said oral care vehicle and said dispersed odor control agent are comprised in dental cream.

20. A method according to claim 17 wherein said oral care vehicle and said odor control agent in admixture are comprised in a portable dose article selected from the group consisting of a lozenge, a mint, a bead, a wafer, a small portable nebulizer containing said admixture in liquid formulated for oral application as a spray, a small portable bottle containing said admixture in liquid formulated for oral application as a drop, and a soft pliable tablet.

21. A method according to claim 17 wherein said oral care vehicle and said dispersed odor control agent are comprised in mouthwash.

* * * * *